US00PP28585P3

(12) United States Plant Patent
Corley

(10) Patent No.: US PP28,585 P3
(45) Date of Patent: Oct. 31, 2017

(54) ***QUERCUS* PLANT NAMED 'CORLEY'S FIRECRACKER'**

(50) Latin Name: *Quercus nuttallii*
Varietal Denomination: CORLEY'S FIRECRACKER

(71) Applicant: Douglas Corley, Monticello, FL (US)

(72) Inventor: Douglas Corley, Monticello, FL (US)

( * ) Notice: Subject to any disclaimer, the term of this patent is extended or adjusted under 35 U.S.C. 154(b) by 76 days.

(21) Appl. No.: 14/757,050

(22) Filed: Nov. 12, 2015

(65) Prior Publication Data

US 2017/0142882 P1 May 18, 2017

(51) Int. Cl.
*A01H 5/00* (2006.01)

(52) U.S. Cl.
USPC ..... Plt./225

(58) Field of Classification Search
USPC ..... Plt./225
See application file for complete search history.

(56) References Cited

PUBLICATIONS

DeGeeter AmongGiants: Guy Sternberg, Oak Guru, Landscape Architecture Magazine Nov. 2014, pp. 156-165.*

* cited by examiner

*Primary Examiner* — June Hwu
(74) *Attorney, Agent, or Firm* — Cassandra Bright

(57) ABSTRACT

A new and distinct *Quercus* cultivar named 'CORLEY'S FIRECRACKER' is disclosed, characterized by having a broad pyramidal, moderately compact growth habit and red new growth, both in Spring and Summer. The new variety is a *Quercus*, normally produced as a small ornamental tree or shrub.

4 Drawing Sheets

Latin name of the genus and species: *Quercus nuttallii*.
Variety denomination: 'CORLEY'S FIRECRACKER'.

BACKGROUND OF THE INVENTION

The new cultivar is a product of chance discovery. The new was discovered as a naturally occurring whole plant mutation from the parent variety *Quercus nuttallii*. The inventor discovered a single plant with bright red foliage growing among a commercial planting of *Quercus nuttallii* at a commercial nursery in Monticello, Fla. The new variety was first selected in Spring of 2007, by the inventor, Douglas Corley.

Asexual reproduction of the new cultivar 'CORLEY'S FIRECRACKER' was first performed at a commercial nursery in Monticello, Fla. by grafting dormant budwood onto *Quercus nuttallii* during May of 2013. Subsequent propagation has shown that the unique features of this cultivar are stable and reproduced true to type on successive generations.

SUMMARY OF THE INVENTION

The cultivar 'CORLEY'S FIRECRACKER' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CORLEY'S FIRECRACKER'. These characteristics in combination distinguish 'CORLEY'S FIRECRACKER' as a new and distinct *Quercus* cultivar:

1. Red foliage color in Spring.
2. Red foliage color in subsequent flushes after Spring
3. Intense red foliage color lasts approximately 1 month.
4. Smaller growth habit than typical of *Quercus nuttallii*.
5. Greyed-Purple branches.

PARENT COMPARISON

Plants of the new cultivar 'CORLEY'S FIRECRACKER' are similar to plants of the parent, *Quercus nuttallii* in most horticultural characteristics, however, plants of the new cultivar 'CORLEY'S FIRECRACKER' have red new foliage. Additionally, plants of the new variety are smaller than those of the parent.

COMMERCIAL COMPARISON

Plants of the new cultivar 'CORLEY'S FIRECRACKER' are similar to plants of the commercial variety *Quercus nuttallii* 'QNSTD' U.S. Plant Pat. No. 16,254 in most horticultural characteristics. However, plants of the new cultivar differ in the following characteristics:

1. 'CORLEY'S FIRECRACKER' branches less densely and at a less acute angle.
2. 'CORLEY'S FIRECRACKER' has new foliage colored near Greyed-Red 182A, heavily flushed Red 53A. The red foliage color of the comparator is Red-Purple 59A
3. Red foliage coloration of 'CORLEY'S FIRECRACKER' persists longer than the red foliage coloration of this comparator.
4. 'CORLEY'S FIRECRACKER' has Greyed-Purple mature petioles, this comparator has Yellow-Green mature petioles Plants of the new cultivar 'CORLEY'S FIRECRACKER' are similar to plants of the commercial variety *Quercus nuttallii* 'QNMTF' U.S. Plant Pat. No. 20,550 in most horticultural characteristics. However, plants of the new cultivar differ in the following characteristics:

1. 'CORLEY'S FIRECRACKER' branches less densely.
2. 'CORLEY'S FIRECRACKER' has new foliage colored near Greyed-Red 182A, heavily flushed Red 53A, the red foliage color of the comparator is Greyed-Purple 183A.
3. Red foliage coloration of 'CORLEY'S FIRECRACKER' persists longer than the red foliage coloration of this comparator.

Plants of the new cultivar 'CORLEY'S FIRECRACKER' are similar to plants of the commercial variety *Quercus petraea×robur* 'Firecracker', unpatented, in some horticultural characteristics. However, plants of the new cultivar differ in the following characteristics:

1. 'CORLEY'S FIRECRACKER' produces much narrower foliage with deeper lobes and dentations.
2. Trees of the new variety are less dense branching, with generally thicker branches than trees of this comparator.

BRIEF DESCRIPTION OF THE PHOTOGRAPH

The accompanying photograph in FIG. 1 illustrates in full color a typical plant of 'FIRECRACKER' grown outdoors, during mid-Spring. Age of the plant photographed is approximately 8 years.

Figure 1:
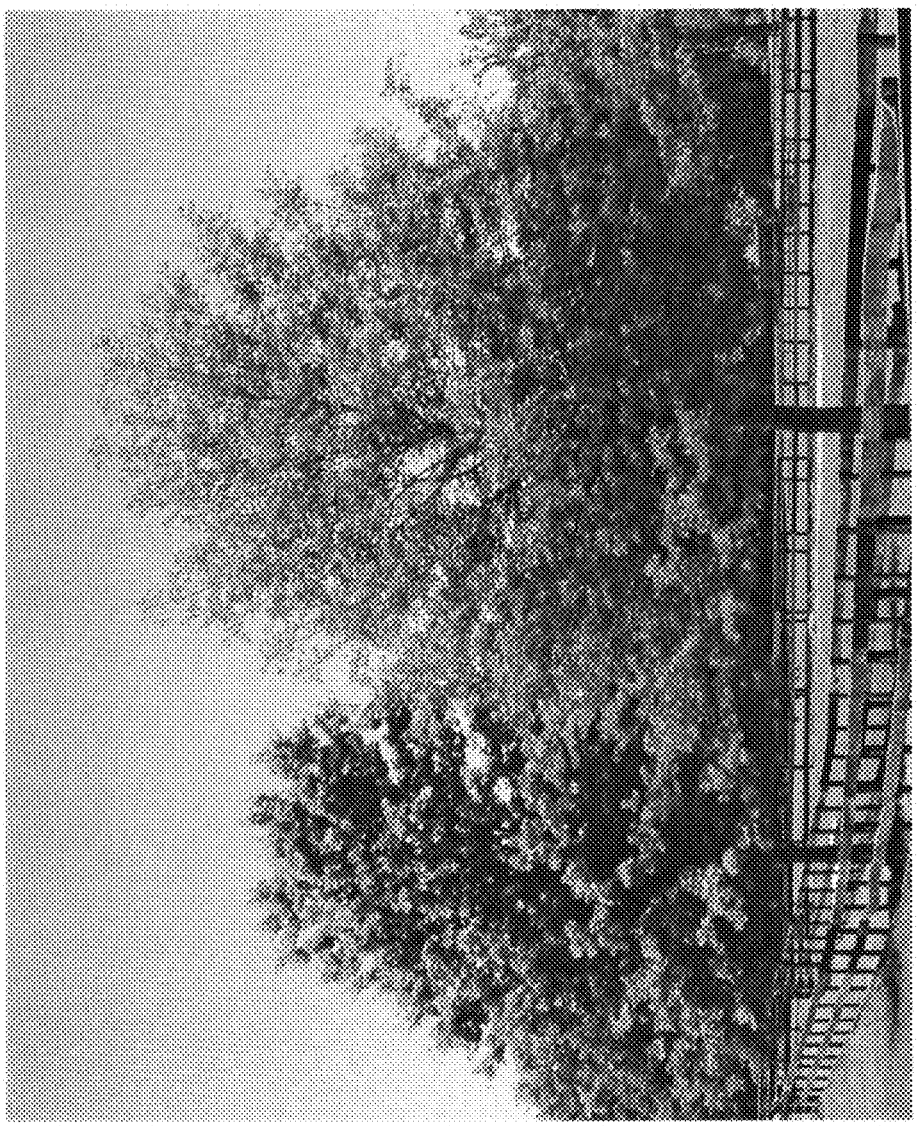
Figure 2:
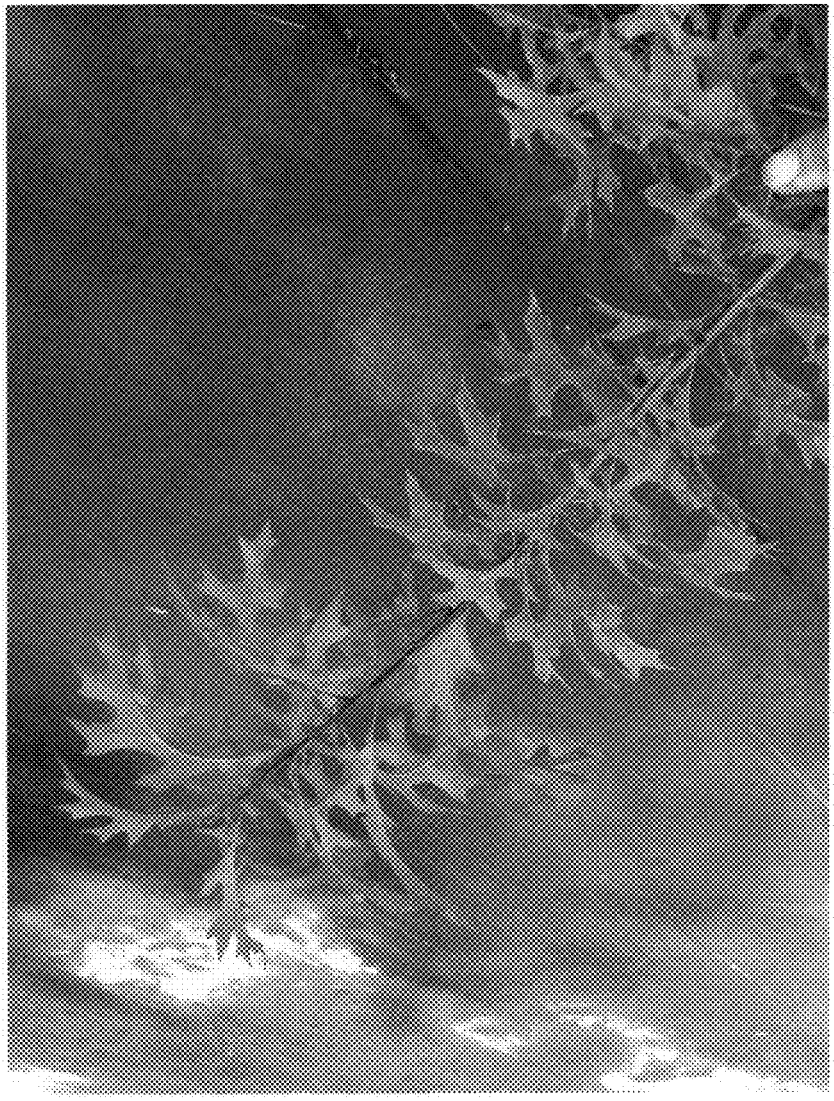
FIG. 2 illustrates Summer new growth of a branch, including both new growth beginning to shift to green, as well as mature green foliage lower on the branch.
Figure 3:
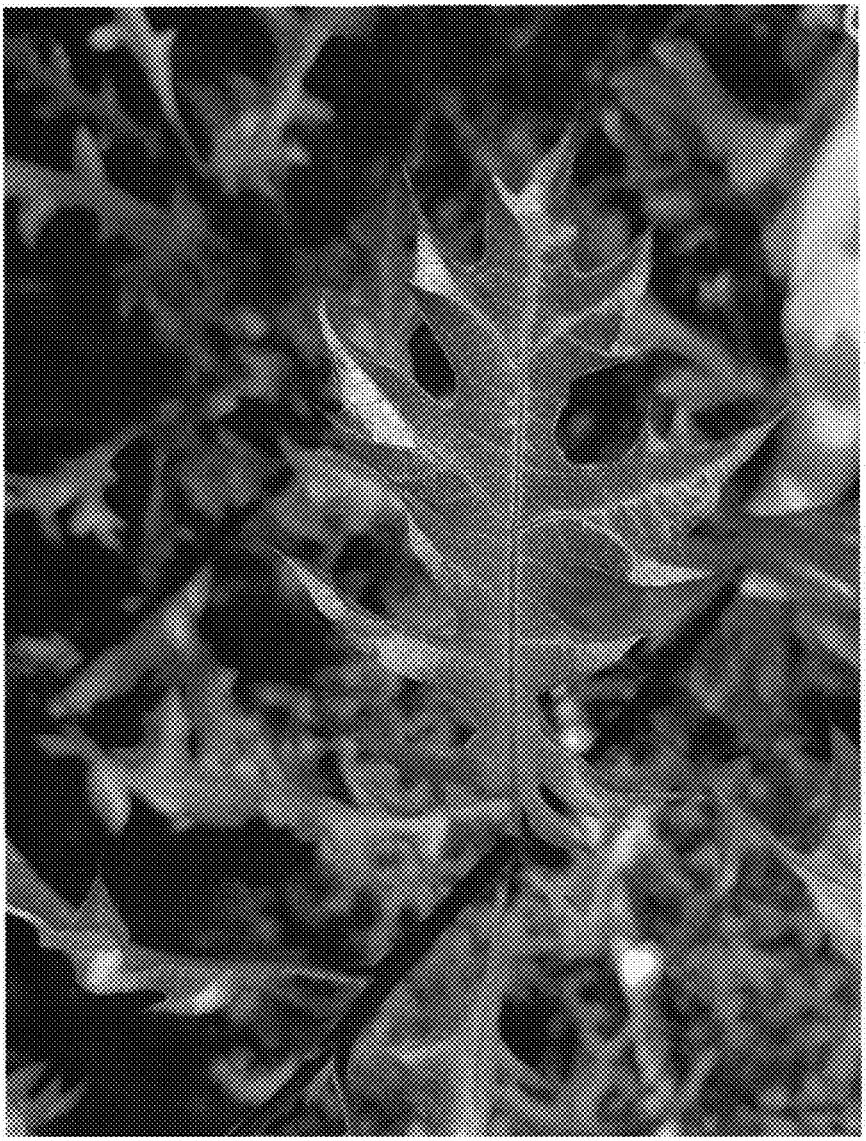
FIG. 3 illustrates the red coloration of new foliage.
Figure 4:
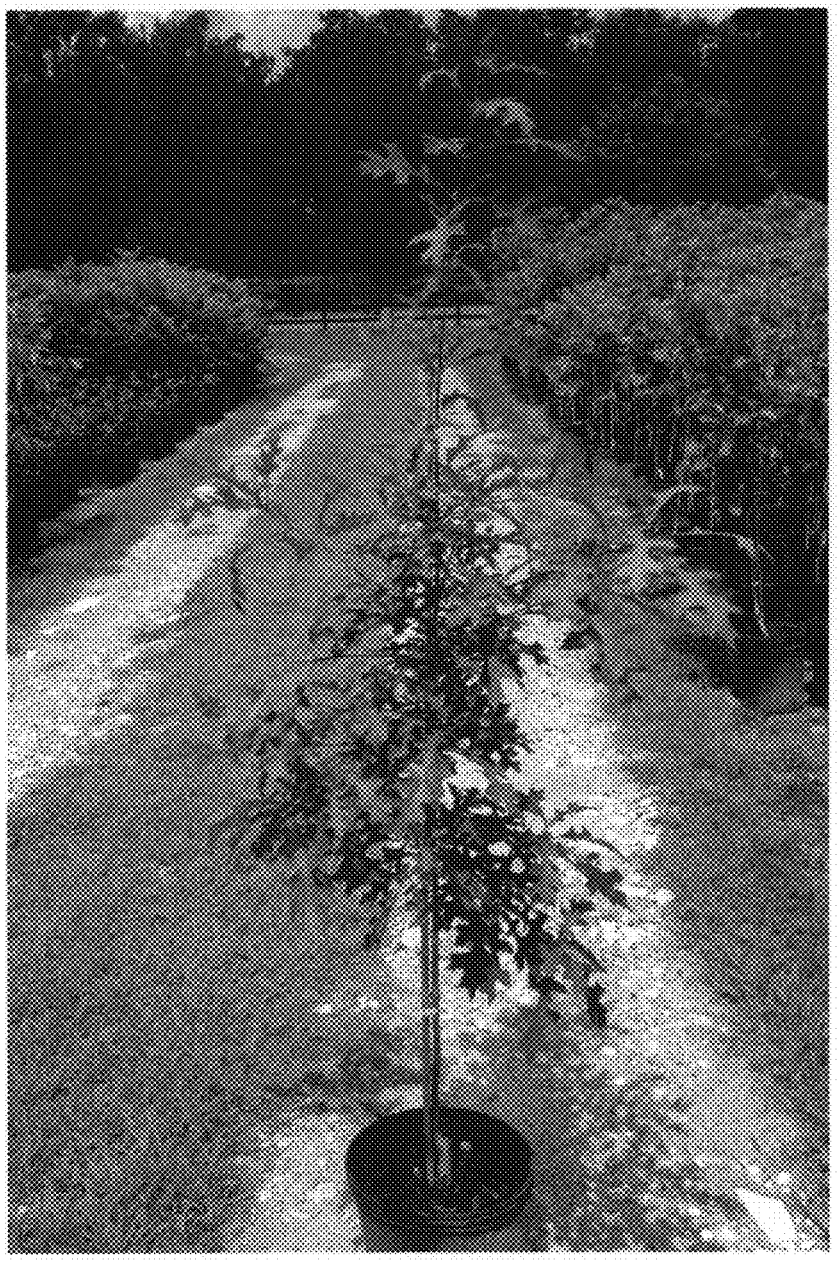
FIG. 4 illustrates a tree of approximately 2 to 3 years old having red new growth, and mature green foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CORLEY'S FIRECRACKER' plants grown outdoors in Monticello, Fla. Growing conditions are similar to USDA Zone 8b. Age of the plants when described is approximately 1 year old. Measurements and numerical values represent averages of typical plant types.

Botanical classification: *Quercus nuttallii* 'CORLEY'S FIRECRACKER'.

PROPAGATION

Time to initiate roots: About 6 to 8 weeks at approximately 24° C.

Root description: Typical *Quercus* root, woody, smaller roots fibrous. Roots brown, color not accurately measured with R.H.S. chart.

PLANT

Growth habit: Broadly pyramidal, medium sized deciduous tree.

Pot size of described plant: 3 gallon pot.

Height: Approximately 1 meter after 1 year.

Plant spread: Approximately 0.5 meters after 1 year.

Branching characteristics: Branching forming approximately 10 cm to 20 cm apart, in an opposite to whorled pattern. Branching angle approximately 45° to 90° from trunk.

Individual branch characteristics (of 1 year old tree):

*Length*.—Up to 25 cm.

*Diameter*.—Up to 0.4 cm.

*Texture*.—Smooth and very slightly glaucous.

*Color*.—Near RHS Greyed-Purple N186A.

Trunk:

*Diameter*.—Approximately 1 cm, after 1 year. Measured approximately 10 cm above the ground.

*Texture*.—Glabrous with lenticels. Glaucous on older trunk, closest to trunk base. Glaucous characteristic reduced on younger trunk, to nearly absent at top. Younger trunk ridged, with scant or no lenticels.

*Color*.—Near RHS Greyed-Purple N186B. Glaucous covering of lower trunk near RHS Greyed-Purple N187D.

*Lenticles*.—Irregular ovate. Approximately 2 to 3 mm long, about 1 mm wide.

FOLIAGE

Leaf:

*Arrangement*.—Alternate, forming a loose spiral.

*Average length*.—Approximately 15.0 to 21.0 cm.

*Average width*.—Approximately 4.5 to 7.0 cm.

*Shape of blade*.—Overall shape elliptic, deeply lobed. Typically 7 to 10 irregularly shaped and sized lobes. Lobe depth average range from approximately 1.5 cm to 3.5 cm. Lobe with average range from approximately 1.0 cm to 3.0 cm.

*Apex*.—Acute to acuminate.

*Base*.—Attenuate.

*Margin*.—Entire.

*Texture of top surface*.—Glabrous, with matte appearance.

*Texture of lower surface*.—Glabrous, with matte appearance.

*Leaf internode length*.—Average range 1.5 cm to 3 cm.

*Color*.—Spring new foliage. Upper side: Near RHS Greyed-Red 182A background, heavily flushed 53A. Under side: Near RHS Red 46C. Mature foliage upper side: Near RHS Green 139A. Mature foliage under side: Near RHS Green 137C. Fall Coloration: No change in coloration observed during the Fall in Monticello, Fla. Dormant Leaf Buds: Shape: Irregular ovate. Size: Average range 4 to 11 mm in length, 3 to 6 mm in diameter. Color: Near RHS Greyed-Purple 183A.

Foliage:

*Venation*.—Type: Pinnate. Color: Young foliage: Venation color upper side: Near RHS Red 53A. Venation color under side: Near RHS Red 46A. Mature foliage: Venation color upper side: Near RHS Greyed-Purple 184A. Venation color under side: Near RHS Green-Yellow 1C. Petiole: Length: Average range 1.0 to 2.5 cm. Diameter: 2 mm. Color Young foliage: Near Red 53A. Mature foliage: Near Greyed-Purple 187B.

FLOWER

General: Monoecious wind pollinate flowers occur in Spring, female flower appear approximately 2 weeks after male catkins.

*Male flowers*.—Catkins, approximately 6 to 14 cm long and 2 to 5 cm wide. Composed of on average 10 to 18 strands of 20 to 60 staminate flowers. Flowers approximately 2 mm in diameter, colored near Yellow-Green N144A.

*Female flowers*.—Inconspicuous, minute, occurring in leaf axils. Flower approximately 2 to 4 mm in diameter, colored near Greyed-Red 178A, turning Greyed-Orange 174A.

OTHER CHARACTERISTICS

Disease/pest resistance: Neither resistance nor susceptibility to pathogens and pests common to *Quercus* have been observed.

Temperature tolerance: The new variety is suitable for growing in USDA zones 5 through 9.

What is claimed is:

1. A new and distinct cultivar of *Quercus* plant named 'CORLEY'S FIRECRACKER' as herein illustrated and described.

* * * * *